United States Patent
Watchtel et al.

(10) Patent No.: US 9,533,112 B2
(45) Date of Patent: Jan. 3, 2017

(54) INHALER

(75) Inventors: Herbert Watchtel, Ingelheim (DE); Achim Moser, Sulzbach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 1310 days.

(21) Appl. No.: 12/138,629

(22) Filed: Jun. 13, 2008

(65) Prior Publication Data

US 2008/0314380 A1    Dec. 25, 2008

(30) Foreign Application Priority Data

Jun. 15, 2007  (EP) ..................................... 07011750
Dec. 11, 2007  (EP) ..................................... 07023920

(51) Int. Cl.
A61M 11/00 (2006.01)
A61M 15/00 (2006.01)
A61M 16/00 (2006.01)
B05B 11/00 (2006.01)

(52) U.S. Cl.
CPC ......... *A61M 15/009* (2013.01); *A61M 15/002* (2014.02); *A61M 15/0021* (2014.02); *A61M 2202/0468* (2013.01); *A61M 2202/064* (2013.01); *B05B 11/0054* (2013.01); *B05B 11/308* (2013.01)

(58) Field of Classification Search
CPC ............ A61M 15/009; A61M 15/0086; A61M 15/0091; A61M 15/0033–15/0041; A61M 2202/064; A61M 2015/0048; A61M 15/0045; A61M 15/0065; A61M 15/00; A61M 15/033–15/041; A61M 15/086; A61M 15/091; A61M 15/065; A61M 15/045

USPC ........... 128/200.14, 200.18–200.23, 203.15, 128/203.19; 222/635, 636, 105, 402.1, 402.2, 222/325

See application file for complete search history.

(56) References Cited

U.S. PATENT DOCUMENTS

| | | | | | |
|---|---|---|---|---|---|
| 2,674,999 | A | * | 4/1954 | Cox ......................... | 128/203.25 |
| 4,291,688 | A | * | 9/1981 | Kistler ..................... | 128/200.23 |
| 4,739,754 | A | * | 4/1988 | Shaner ..................... | 128/203.15 |
| 4,846,168 | A | * | 7/1989 | Abiko et al. ............. | 128/203.15 |
| 4,926,852 | A | * | 5/1990 | Zoltan et al. ............. | 128/200.23 |
| 4,951,659 | A | * | 8/1990 | Weiler et al. ............ | 128/200.18 |
| 5,349,944 | A | * | 9/1994 | Chippendale et al. .. | 128/200.14 |
| 5,435,282 | A | * | 7/1995 | Haber et al. ............. | 128/200.16 |
| 5,497,944 | A | | 3/1996 | Weston et al. | |
| 5,568,807 | A | * | 10/1996 | Mecikalski .............. | 128/203.21 |
| 5,672,581 | A | | 9/1997 | Rubsamen et al. | |
| 5,964,416 | A | | 10/1999 | Jaeger et al. | |
| 6,065,472 | A | * | 5/2000 | Anderson et al. ....... | 128/203.21 |

(Continued)

FOREIGN PATENT DOCUMENTS

| | | | |
|---|---|---|---|
| CA | 2 297 174 A1 | 2/1999 | |
| EP | 1 003 478 B1 | 5/2000 | |

(Continued)

*Primary Examiner* — Tan-Uyen (Jackie) T Ho
*Assistant Examiner* — Ned T Heffner
(74) *Attorney, Agent, or Firm* — David S. Safran (57) ABSTRACT

An active inhaler for delivery of an inhalation formulation has an overall flow resistance of at least 60,000 $Pa^{1/2}$ $s/m^3$ for ambient air drawn into a mouthpiece of the inhaler. This flow resistance when air and the aerosol are sucked via the mouthpiece is produced by the sizing of at least on air supply opening and/or an insert within the mouthpiece.

20 Claims, 4 Drawing Sheets

(56) References Cited

U.S. PATENT DOCUMENTS

| | | | |
|---|---|---|---|
| 6,166,237 A | 12/2000 | Simandan et al. | |
| 6,176,237 B1* | 1/2001 | Wunderlich et al. | 128/203.12 |
| 6,293,279 B1* | 9/2001 | Schmidt et al. | 128/200.23 |
| 6,615,826 B1* | 9/2003 | Gabrio et al. | 128/200.23 |
| 6,631,721 B1* | 10/2003 | Salter et al. | 128/203.21 |
| 6,701,922 B2* | 3/2004 | Hindle et al. | 128/203.27 |
| 6,718,969 B1* | 4/2004 | Rubin et al. | 128/200.14 |
| 6,748,949 B2* | 6/2004 | Smaldone | 128/203.29 |
| 6,779,521 B1* | 8/2004 | Schmehl et al. | 128/203.12 |
| 6,848,443 B2* | 2/2005 | Schmidt et al. | 128/200.23 |
| 7,571,722 B2* | 8/2009 | Wuttke et al. | 128/200.14 |
| 2005/0183718 A1* | 8/2005 | Wuttke et al. | 128/200.14 |
| 2005/0205087 A1* | 9/2005 | Kablik et al. | 128/200.23 |

FOREIGN PATENT DOCUMENTS

| | | |
|---|---|---|
| WO | 91/14468 A1 | 10/1991 |
| WO | 97/12687 A1 | 4/1997 |
| WO | 00/21594 A2 | 4/2000 |
| WO | 03/084502 A1 | 10/2003 |

* cited by examiner

INHALER

BACKGROUND OF THE INVENTION

Field of Invention

The present invention relates to an inhaler.

Description of Related Art

The present invention specifically relates to active inhalers such as an inhaler sold by the assignee of the present application under the trademark RESPIMAT®, as illustrated in its basic structure in WO 91/14468 A1 (corresponding to U.S. Pat. No. 5,497,944) and in a specific embodiment in WO 97/12687 A1 (corresponding to U.S. Pat. No. 5,964, 416; FIGS. 6a, 6b). The inhaler has, as a reservoir for a fluid which is to be atomized, an insertable rigid container having an inner bag containing the fluid and a pressure generator with a drive spring for delivering and atomizing the fluid.

The invention also relates to powder inhalers, whether multidose pre-metered or reservoir devices.

To supplement the disclosure of the present application reference is made to the complete disclosure of both U.S. Pat. Nos. 5,497,944 and 5,964,416. Generally, the disclosure contained therein preferably relates to a inhaler with a spring pressure of 5 to 200 MPa, preferably 10 to 100 MPa on the fluid, with a volume of fluid delivered per stroke of 10 to 50 µl, preferably 10 to 20 µl, most preferably about 15 µl. The fluid is converted into an aerosol the droplets of which have an aerodynamic diameter of up to 20 µm, preferably 3 to 10 µm. Furthermore, the disclosure contained therein preferably relates to a inhaler of cylindrical shape about 9 cm to about 15 cm and about 2 cm to about 5 cm wide and with a jet spray angle of 20° to 160°, preferably 80° to 100°. These values also apply to the inhaler according to the teaching of the present invention as particularly preferred values.

Active inhalers in the sense of the present invention generate the desired aerosol of the inhalation formulation by means of a conveying means, such as a propellant, a pump, an air pump or any other pressure generator or compressed or liquefied gas, i.e., not due to an air stream of a patient or user who breathes in, although the dispensing operation (aerosol operation) can be triggered by the breathing in.

When a patient puts a mouthpiece or any other end piece in his mouth and breathes in, an air stream of ambient air is sucked through the inhaler to entrain the already generated aerosol of the inhalation formulation and to discharge this aerosol. A pressure drop occurs within the inhaler when the air stream flows through the inhaler. This pressure drop depends on the flow rate and flow velocity. The flow resistance represents a quantity relating to the square root of the pressure drop at a certain flow rate. In the context of the present invention, the term "flow resistance" means the resistance which occurs when air is sucked from the mouthpiece or any other end piece of the inhaler during inhalation. In particular, the flow resistance relates to a flow path for ambient air through at least one air supply opening of the inhaler into a mouthpiece of the inhaler. More preferably, the flow resistance means the total flow resistance of the inhaler in the present invention, even if the inhaler has multiple air supply openings through which air can be sucked into the mouthpiece.

In contrast to active inhalers, where an active means generates the aerosol, passive inhalers usually have a higher flow resistance for the patient or user. This results from the fact that the generation of aerosol requires energy and, thus, leads to a respective flow resistance in passive inhalers. Nevertheless, it has been an object of the previous developments to keep the flow resistance as low as possible in both types of inhalers in order to facilitate inhalation for the patient or user.

SUMMARY OF THE INVENTION

A primary object of the present invention is to provide an active inhaler with optimized discharge characteristics.

The above object is achieved by an inhaler having a flow resistance of at least 60,000 $Pa^{1/2}$ s/m³. In particular, the object is achieved by the inhaler having an insert in the mouthpiece in order to define or increase the flow resistance and/or to guide a flow of air entering through the at least one air supply opening.

Figure 1:
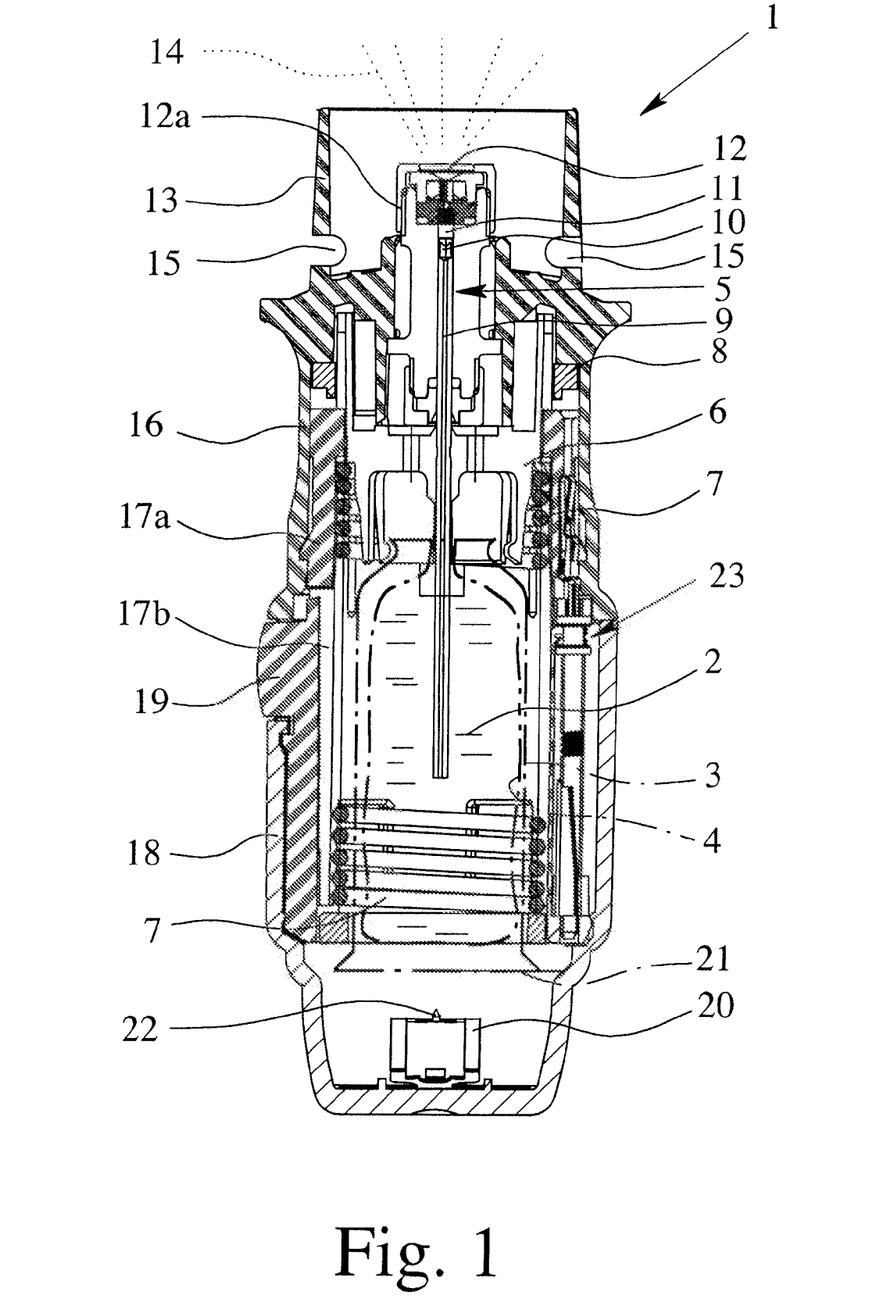
Figure 2:
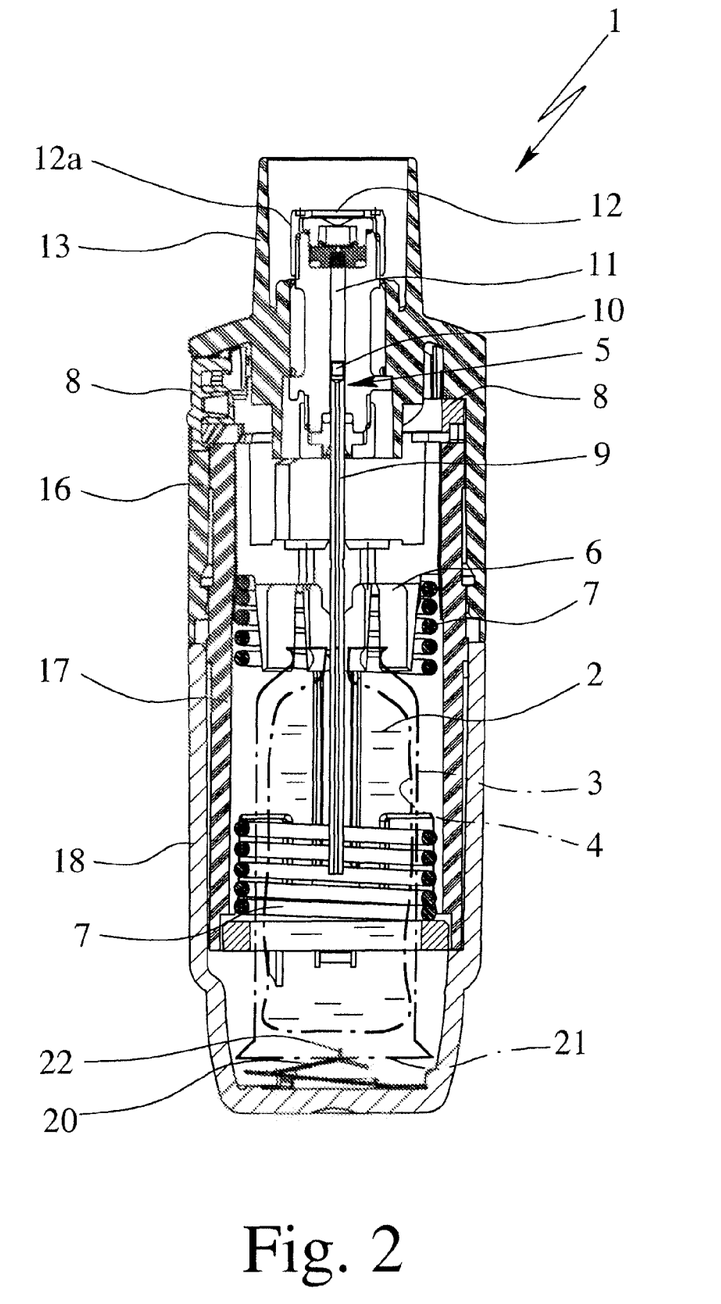

A principal aspect of the present invention is that the flow resistance of the inhaler is increased to a significantly higher level than in previous inhalers of the present type. Such inhalers usually have a flow resistance of only about 16,000 $Pa^{1/2}$ $s/m^3$ as contrasted with at least 60,000 $Pa^{1/2}$ $s/m^3$ in accordance with the present invention.

The increased flow resistance results in optimized discharged characteristics of the inhaler. Due to the higher flow resistance the patient or user will breathe in more slowly so that the total inhalation time is increased. In particular, the higher flow resistance makes it easier for the patient or user to slowly breathe in. This applies to intuitive breathing as well as to willful breathing. Thus, a lower flow velocity can be achieved in the mouth and pharynx region which results in lower impaction of the aerosol particles (inhalation formulation) in this region so that the percentage of lung deposition of the inhalation formulation is increased.

According to another aspect of the present invention, the inhaler comprises an insert in the mouthpiece in order to define or increase the flow resistance and/or to adapt or guide the flow of bypass air. This allows optimized discharge characteristics.

Further aspects, features, properties and advantages of the present invention are described in the subsequent description of a preferred embodiment with reference to the accompanying drawings.

BRIEF DESCRIPTION OF THE DRAWINGS

FIG. 1 is a schematic sectional view of an inhaler in the non-tensioned state;

FIG. 2 is a schematic sectional view of the inhaler in the tensioned state rotated by 90° as compared with FIG. 1;

FIG. 3*a* schematically shows an insert, which can be mounted or inserted in a mouthpiece of the inhaler in a plan view;

FIG. 3*b* is a schematic side view of the insert according to FIG. 3*a;*

FIG. 3*c* is schematic side view of the insert as seen from a direction perpendicular to the view according to FIG. 3*b;*

FIG. 3*d* is a schematic sectional view of the insert taken along line IIIb-IIIb of FIG. 3*a*; and FIG. 4 is a schematic sectional view of the inhaler with the insert.

DETAILED DESCRIPTION OF THE INVENTION

In the figures, the same reference numbers are used for identical or similar parts, even if a repeated description is omitted. In particular, identical or corresponding advantages and properties then also result or may be achieved.

FIGS. 1 & 2 show an inhaler 1 according to the present invention for atomizing an inhalation formulation 2 as an aerosol, particularly a highly effective pharmaceutical composition or the like, diagrammatically shown in the active state (FIG. 1) and in the active state (FIG. 2).

The term "aerosol" in this respect is not limited to an inhalation formulation in liquid from, but also encompasses powder formulations.

FIGS. 3 and 4 show an insert 24 for an inhaler 1. The insert 24 can be inserted in the mouthpiece 13 of the inhaler.

The inhaler 1 is constructed, in particular, as a portable inhaler and preferably operates without propellant gas. However, the present invention may also be applied to inhalers 1 using a propellant, such as so-called MDIs (metered dose inhalers), a gas, such as compressed or liquefied gas or air, or the like, i.e., in particular, to all kind of inhalers 1.

The inhalation formulation 2 is preferably a liquid, in particular, a solution, suspension or suslution (mixture of solution and suspension), but can have any form and can be, e.g., a powder or the like.

When the inhalation formulation 2, preferably a liquid, more particularly, a pharmaceutical composition, is nebulized, an aerosol is formed, which can be breathed in or inhaled by a user (not shown). Usually the inhaling is done at least once a day, more particularly several times a day, preferably at set intervals, depending on the complain from which the patient is suffering.

The inhaler 1 has in particular an insertable and preferably exchangeable container 3 containing the inhalation formulation 2. The container thus forms a reservoir for the inhalation formulation 2 which is to be nebulized. Preferably, the container 3 contains an amount of inhalation formulation 2 or active substance which is sufficient to provide up to 200 dosage units, for example, i.e., to allow up to 200 sprays or applications. A typical container 3, as disclosed in U.S. Pat. No. 5,964,416, holds a volume of about 2 to 10 ml.

The container 3 is substantially cylindrical or cartridge-shaped and once the inhaler 1 has been opened, the container can be inserted therein from below and changed if desired. The container 3 is preferably of rigid construction, the inhalation formulation 2, in particular, being held in a collapsible bag 4 in the container 3.

The inhaler 1 has a conveying means, such as a propellant, a pump, an air pump or any other pressure generator or compressed or liquefied gas, in particular a pump or pressure generator 5 for conveying gas, any other fluid and/or the inhalation formulation 2 and for nebulizing the inhalation formulation 2, particularly in a preset and optionally adjustable dosage amount.

The inhalation formulation 2 may be metered in the inhaler 1 as it is the case in the present embodiment or may be pre-metered in an appropriate storage means, such as a blister with multiple blister pockets or the like.

In the present embodiment, the pressure generator 5 has preferably a holder 6 for the container 3, an associated drive spring 7, only partly shown, with a locking element 8 which can be manually operated to release it, a conveying tube 9 with a non-return valve 10, a pressure chamber 11 and/or an expulsion nozzle 12 in the region of a mouthpiece 13. The container 3 is fixed in the inhaler 1 via the holder 6 such that the conveying tube 9 penetrates into the container 3. The holder 6 may be constructed so that the container 3 is able to be exchanged.

As the drive spring 7 is axially tensioned the holder 6 with the container 3 and the conveying tube 9 is moved downwards in the drawings, and the inhalation formulation 2 is sucked out of the container 3 into the pressure chamber 11 of the pressure generator 5 through the non-return valve 10.

During the subsequent relaxation after actuation of the locking element 8 the inhalation formulation 2 in the pressure chamber 11 is put under pressure as the conveying tube 9 with its now closed non-return valve 10 is moved back upwards by the relaxation of the drive spring 7 and now acts as a pressing ram or piston. This pressure forces the inhalation formulation 2 through the expulsion or dispensing nozzle 12, whereupon it is nebulized into an aerosol 14, as shown in FIG. 1. The droplet size of the particles for a device of the RESPIMAT® type has already been discussed hereinbefore.

A user (not shown) can inhale the aerosol 14, while an air supply is sucked into the mouthpiece 13 through at least one air supply opening 15, preferably multiple air supply openings 15. Thus, a bypass is formed so that ambient air can be sucked into the mouthpiece 13.

The inhaler 1 comprises an upper housing part 16 and an inner part 17 which is rotatable relative thereto (FIG. 2) having an upper part 17*a* and a lower part 17*b* (FIG. 1), while an in particular manually operable housing part 18 is releasably fixed, particularly fitted onto the inner part 17, preferably by means of a retaining element 19. In order to insert and/or replace the container 3 the housing part 18 can be detached from the inhaler 1.

The inhaler 1 further comprises one or more air supply openings 15 with a reduced size compared to the state of the art. Alternatively or additionally, an insert 14 can be inserted in the mouthpiece 13 of the inhaler 1 as explained later.

The housing part 18 can be rotated relative to the upper housing part 16, carrying with it the part 17*b* of the inner part 17 which is lower down in the drawings. As a result the drive spring 7 is tensioned in the axial direction by means of a gear (not shown) acting on the holder 6. During tensioning, the container 3 is moved axially downwards until the container 3 assumes an end position as shown in FIG. 2. In this state, the drive spring 7 is under tension having been compressed. During the nebulizing process, the container 3 is moved back into its original position by the drive spring 7. Thus, the container 3 executes a lifting movement during the tensioning process and during the atomizing process.

The housing part 18 preferably forms a cap-like lower housing part and fits around or over a lower free end portion of the container 3. As the drive spring 7 is tensioned, the container 3 moves with its end portion (further) into the housing part 18 or towards the end face thereof, while an axially acting spring 20 arranged in the housing part 18 comes to bear on the base 21 of the container and pierces the container 3 or a base seal thereon with a piercing element 22 when the container makes contact with it for the first time, to allow air in.

The inhaler 1 has a monitoring device (not shown) which counts the actuations of the inhaler 1, preferably by detecting the rotation of the inner part 17 relative to the upper part 16 of the housing, such as that shown and described in U.S. Pat. No. 5,964,416 referenced above.

The total size of the air supply opening(s) 15 (at least essentially) defines or sets the flow resistance of the inhaler 1 when a user (not shown) puts the mouthpiece 13 in his mouth and breathes in to inhale the aerosol 14. This size is significantly reduced according to the present invention. Therefore, the inhaler 1 has a flow resistance of at least 60,000 $Pa^{1/2}$ $s/m^3$, in particular, of at least 75,000 $Pa^{1/2}$ $s/m^3$, more preferably about 90,000 or 96,000 $Pa^{1/2}$ $s/m^3$ or more.

The flow resistance is measured here as the quotient of the square root of the pressure drop divided by the flow rate. For example, a pressure drop of 4,000 Pa results in a flow resistance of 97301 $Pa^{1/2}$ $s/m^3$ at a flow rate of 39 l/min.

Thus, a relatively slow inhalation can be achieved. In particular, the duration of the inhalation can be prolonged and/or a relatively low flow velocity or rate through the mouthpiece 8 or its outlet tube 18 can be achieved, even if the patient or user breaths in only intuitively.

In order to define or increase the flow resistance as mentioned above, the at least one air supply opening 15 or multiple air supply openings 15 may be reduced in cross section. In particular, the following diameters may be chosen, wherein the diameter relate to a circular aerodynamic cross section corresponding in its effect to the actual cross section of the respective opening 15: diameter 3.6 to 3.2 mm, if the inhaler comprises only a single opening 15; diameter 2.6 to 2.2 mm, if the inhaler 1 comprises two openings 15; diameter 2.1 to 1.8 mm, if the inhaler 1 comprises three openings 15; diameter 1.8 to 1.5 mm, when the inhaler 1 has four openings 15. Thus, a (total) flow resistance of the flow path of ambient air into the mouthpiece of at least about 60,000 $pa^{1/2}$ $s/m^3$ to 96,000 $pa^{1/2}$ $s/m^3$ can be achieved.

Figures 3A, 3B:
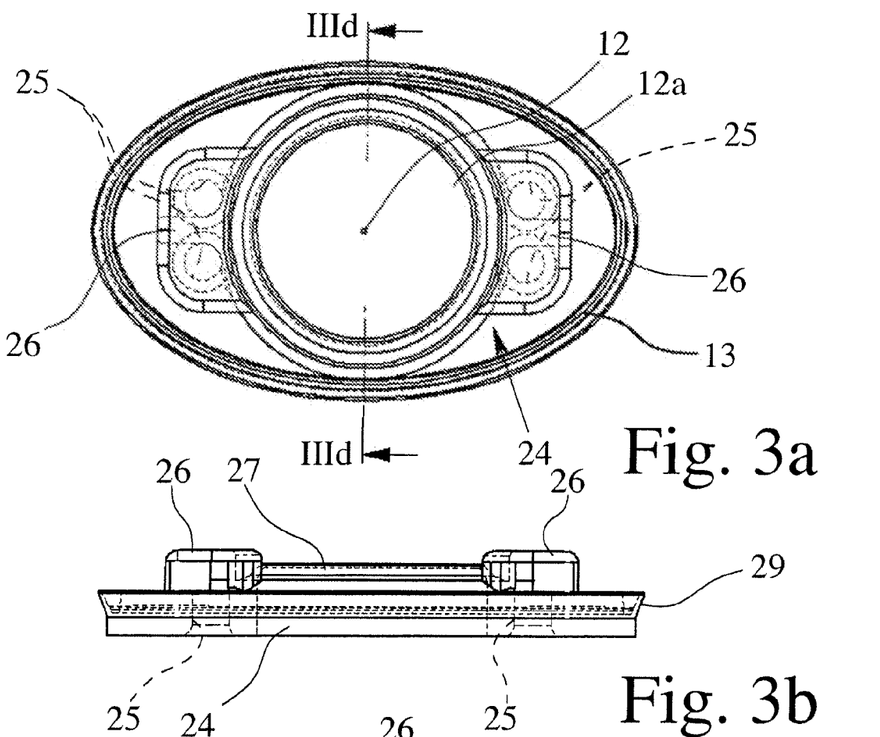
Figures 3C, 3D:
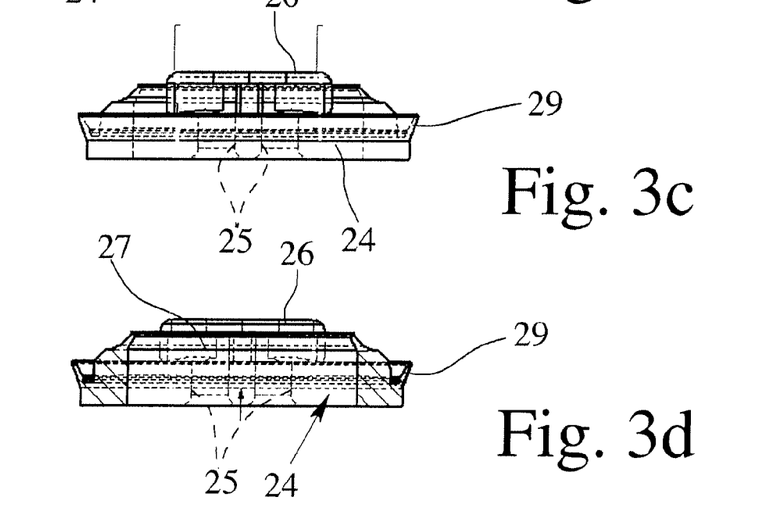
Figure 4:
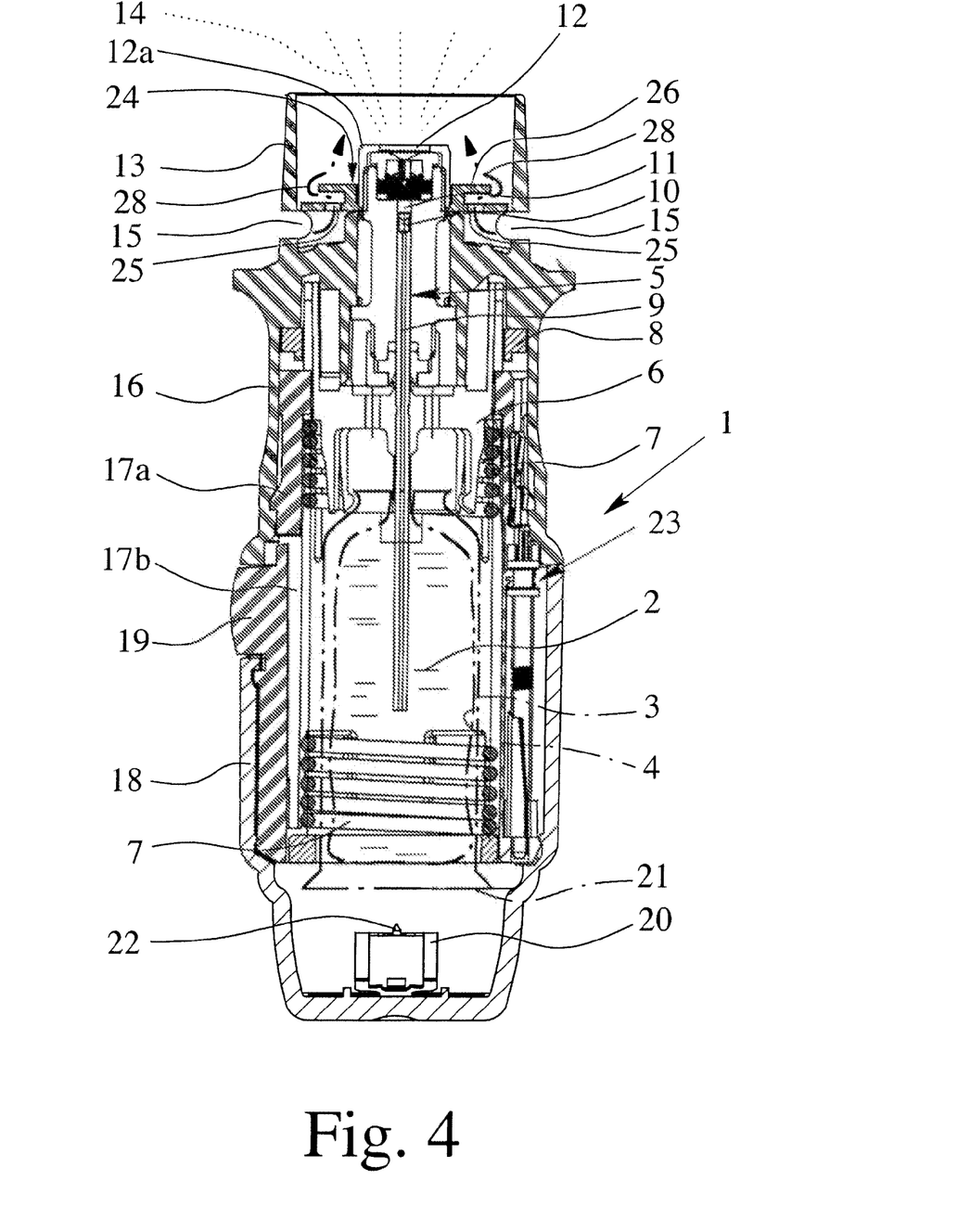

As already mentioned, an insert 24 may be used to define or increase the flow resistance as mentioned above, and/or to create a device flow path 28 or flow characteristics as explained later. FIG. 3a shows a view into the open mouthpiece 13 of the inhaler 1 with the insert 24. FIGS. 3b to 3d show different views of the insert 24. FIG. 4 shows a schematic section of the inhaler 1 with the insert 24.

The insert 24 is inserted into the mouthpiece 13, preferably sealingly between the inner wall of the mouthpiece 13 and a nozzle protrusion 12a. The nozzle protrusion 12a preferably protrudes into the mouthpiece 13 and/or is preferably at least essentially cylindrical. The nozzle protrusion 12a preferably holds or forms the nozzle 12. However, other constructional solutions are possible as well.

The illustrated insert 24 is essentially flat or plate-like. However, other constructional solutions are possible as well.

The insert 24 preferably comprises a central opening 27 for mounting the insert 24 over the nozzle protrusion 12a in order to allow the preferred mounting between the outer or peripheral surface of the nozzle protrusion 12a and the inner surface of the mouthpiece 13.

Preferably, the insert 24 is clamped into the mouthpiece 13 as described. However, it can be fastened in any suitable manner.

Preferably, the insert 24 comprises at least one parallel sealing lip 29 to avoid any undesired bypass flow and/or to achieve a desired clamping within the mouthpiece 13. However, the insert 24 can also be press-fitted into the mouthpiece 13 and/or onto the nozzle protrusion 12a.

The insert 24 preferably comprises at least one hole 25, in the illustrated embodiment, four holes 25, through which ambient air, which has been sucked in through the openings 15, can flow.

The air stream 28 of bypass air flowing through the at least one hole 25 or any other opening is preferably deflected or guided preferably by the insert 24 in order slow down the flow velocity, and/or to generate turbulences, and/or to allow optimized guidance of the aerosol 14 into the mouth of a user (not shown), and/or to allow optimized mixing of the bypass or ambient air with the aerosol 14.

In the illustrated embodiment, the insert 24 comprises at least one guiding element 26, here two guiding elements 26, which deflect(s) the air flow (schematically shown in FIG. 4) through the associated hole(s) 25 in the desired manner. In particular, the guiding element 26 blocks a direct or straight flow of the bypass or ambient air through the mouthpiece 13. In the present embodiment, the guiding element 26 is spaced relative to its associated hole(s) 25 and/or covers the associated hole(s) 25 and/or extends essentially transversally relative to the main flow direction or outlet direction of the inhaler 1.

The at least one hole 25 may be used to define or increase the total flow resistance of the inhaler 1 as mentioned above and/or to create a device flow path 28 or desired flow characteristics. In particular, the at least one hole 25 may comprise an aerodynamic cross section with a diameter depending on the number of the holes 25 and dimensioned as mentioned above for the openings 15, e.g., in case of four holes 25, each hole 25 preferably has an aerodynamic cross section with a diameter of about 1.8 to 1.5 mm. If the holes 15 form the throttle, and, thus, define the flow restriction, the insert with holes 25 is not necessary. However, if the openings 15 are very large, then, the insert with the holes 25 is needed and the flow resistance will, for the most part, depend only the size and number of holes 25.

In the illustrated embodiment, two guiding elements 26 are provided, each of which covers or is associated with two holes 25. However, other constructional solutions are possible as well.

The insert 24 may be optionally mounted. Additionally or alternatively, different inserts 24 can be mounted depending on the respective inhalation formulation 2 to achieve the desired results. In particular, to adapt the flow resistance and/or characteristic of the bypass air to the respective inhalation formulation 2.

Preferably, the inhaler 1 is portable, works only mechanically and/or is hand-held.

Some preferred ingredients and/or compositions of the preferably medicinal formulation 2 are listed below. As already mentioned, they are in particular powders or liquids in the broadest sense. Particularly preferably the formulation 2 contains the following:

The compounds listed below may be used in the device according to the invention on their own or in combination. In the compounds mentioned below, W is a pharmacologically active substance and is selected (for example) from among the betamimetics, anticholinergics, corticosteroids, PDE4-inhibitors, LTD4-antagonists, EGFR-inhibitors, dopamine agonists, H1-antihistamines, PAF-antagonists and PI3-kinase inhibitors. Moreover, double or triple combinations of W may be combined and used in the device according to the invention. Combinations of W might be, for example:

W denotes a betamimetic, combined with an anticholinergic, corticosteroid, PDE4-inhibitor, EGFR-inhibitor or LTD4-antagonist, W denotes an anticholinergic, combined with a betamimetic, corticosteroid, PDE4-inhibitor, EGFR-inhibitor or LTD4-antagonist, W denotes a corticosteroid, combined with a PDE4-inhibitor, EGFR-inhibitor or LTD4-antagonist W denotes a PDE4-inhibitor, combined with an EGFR-inhibitor or LTD4-antagonist W denotes an EGFR-inhibitor, combined with an LTD4-antagonist.

The compounds used as betamimetics are preferably compounds selected from among albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248 and 3-(4-{6-[2-hydroxy-2-(4-hydroxy-3-hydroxymethyl-phenyl)-ethylamino]-hexyloxy}-butyl)-benzyl-sulphonamide 5-[2-(5,6-diethyl-indan-2-ylamino)-1-hydroxy-ethyl]-8-hydroxy-1H-quinolin-2-one 4-hydroxy-7-[2-{[2-{[3-(2-phenylethoxy)propyl] sulphonyl}ethyl]-amino}ethyl]-2(3H)-benzothiazolone 1-(2-fluoro-4-hydroxyphenyl)-2-[4-(1-benzimidazolyl)-2-methyl-2-butylamino]ethanol 1-[3-(4-methoxybenzyl-amino)-4-hydroxyphenyl]-2-[4-(1-benzimidazolyl)-2-methyl-2-butylamino]ethanol 1-[2H-5-hydroxy-3-oxo-4H-1,4-benzoxazin-8-yl]-2-[3-(4-N,N-dimethylaminophenyl)-2-methyl-2-propylamino] ethanol 1-[2H-5-hydroxy-3-oxo-4H-1,4-benzoxazin-8-yl]-2-[3-(4-methoxyphenyl)-2-methyl-2-propylamino]ethanol 1-[2H-5-hydroxy-3-oxo-4H-1,4-benzoxazin-8-yl]-2-[3-(4-n-butyloxyphenyl)-2-methyl-2-propylamino]ethanol 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol 5-hydroxy-8-(1-hydroxy-2-isopropylaminobutyl)-2H-1,4-benzoxazin-3-(4H)-one 1-(4-amino-3-chloro-5-trifluoromethylphenyl)-2-tert.-butylamino)ethanol 6-hydroxy-8-{1-hydroxy-2-[2-(4-methoxy-phenyl)-1,1-dimethyl-ethylamino]-ethyl}-4H-benzo[1,4]oxazin-3-one 6-hydroxy-8-{1-hydroxy-2-[2-(ethyl 4-phenoxy-acetate)-1,1-dimethyl-ethylamino]-ethyl}-4H-benzo[1,4]oxazin-3-one 6-hydroxy-8-{1-hydroxy-2-[2-(4-phenoxy-acetic acid)-1,1-dimethyl-ethylamino]-ethyl}-4H-benzo[1,4]oxazin-3-one 8-{2-[1,1-dimethyl-2-(2,4,6-trimethylphenyl)-ethylamino]-1-hydroxy-ethyl}-6-hydroxy-4H-benzo[1,4]oxazin-3-one 6-hydroxy-8-{1-hydroxy-2-[2-(4-hydroxy-phenyl)-1,1-dimethyl-ethylamino]-ethyl}-4H-benzo[1,4]oxazin-3-one 6-hydroxy-8-{1-hydroxy-2-[2-(4-isopropyl-phenyl)-1,1-dimethyl-ethylamino]-ethyl}-4H-benzo[1,4]oxazin-3-one 8-{2-[2-(4-ethyl-phenyl)-1,1-dimethyl-ethylamino]-1-hydroxy-ethyl}-6-hydroxy-4H-benzo[1,4]oxazin-3-one 8-{2-[2-(4-ethoxy-phenyl)-1,1-dimethyl-ethylamino]-1-hydroxy-ethyl}-6-hydroxy-4H-benzo[1,4]oxazin-3-one 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid 8-{2-[2-(3,4-difluoro-phenyl)-1,1-dimethyl-ethylamino]-1-hydroxy-ethyl}-6-hydroxy-4H-benzo[1,4]oxazin-3-one 1-(4-ethoxy-carbonylamino-3-cyano-5-fluorophenyl)-2-(tert-butylamino)ethanol 2-hydroxy-5-(1-hydroxy-2-{2-[4-(2-hydroxy-2-phenyl-ethylamino)-phenyl]-ethylamino}-ethyl)-benzaldehyde N-[2-hydroxy-5-(1-hydroxy-2-{2-[4-(2-hydroxy-2-phenyl-ethylamino)-phenyl]-ethylamino}-ethyl)-phenyl]-formamide 8-hydroxy-5-(1-hydroxy-2-{2-[4-(6-methoxy-biphenyl-3-ylamino)-phenyl]-ethylamino}-ethyl)-1H-quinolin-2-one 8-hydroxy-5-[1-hydroxy-2-(6-phenethylamino-hexylamino)-ethyl]-1H-quinolin-2-one 5-[2-(2-{4-[4-(2-amino-2-methyl-propoxy)-phenylamino]-phenyl}1-ethylamino)-1-hydroxy-ethyl]-8-hydroxy-1H-quinolin-2-one

[3-(4-{6-[2-hydroxy-2-(4-hydroxy-3-hydroxymethyl-phenyl)-ethylamino]-hexyloxy}-butyl)-5-methyl-phenyl]-urea 4-(2-{6-[2-(2,6-dichloro-benzyloxy)-ethoxy]-hexylamino}-1-hydroxy-ethyl)-2-hydroxymethyl-phenol 3-(4-{6-[2-hydroxy-2-(4-hydroxy-3-hydroxymethyl-phenyl)-ethylamino]-hexyloxy}-butyl)-benzylsulphonamide 3-(3-{7-[2-hydroxy-2-(4-hydroxy-3-hydroxymethyl-phenyl)-ethylamino]-heptyloxy}-propyl)-benzylsulphonamide

4-(2-{6-[4-(3-cyclopentanesulphonyl-phenyl)-butoxy]-hexylamino}-1-hydroxy-ethyl)-2-hydroxymethyl-phenol N-Adamantan-2-yl-2-(3-{2-[2-hydroxy-2-(4-hydroxy-3-hydroxymethyl-phenyl)-ethylamino]-propyl}-phenyl)-acetamide optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The anticholinergics used are preferably compounds selected from among the tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine. In the above-mentioned salts the cations are the pharmacologically active constituents. As anions the above-mentioned salts may preferably contain the chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts the chlorides, bromides, iodides and methanesulphonates are particularly preferred.

Other preferred anticholinergics are selected from among the salts of formula AC-1

AC-1 wherein X⁻ denotes an anion with a single negative charge, preferably an anion selected from among the fluoride, chloride, bromide, iodide, sulphate, phosphate, methanesulphonate, nitrate, maleate, acetate, citrate, fumarate, tartrate, oxalate, succinate, benzoate and p-toluenesulphonate, preferably an anion with a single negative charge, particularly preferably an anion selected from among the fluoride, chloride, bromide, methanesulphonate and p-toluenesulphonate, particularly preferably bromide, optionally in the form of the racemates, enantiomers or hydrates thereof. Of particular importance are those pharmaceutical combinations which contain the enantiomers of formula AC-1-en

AC-1-en wherein X⁻ may have the above-mentioned meanings. Other preferred anticholinergics are selected from the salts of formula AC-2

AC-2 wherein R denotes either methyl or ethyl and wherein X⁻ may have the above-mentioned meanings. In an alternative embodiment the compound of formula AC-2 may also be present in the form of the free base AC-2-base.

AC-2-base

Other specified compounds are:
tropenol 2,2-diphenylpropionate methobromide,
scopine 2,2-diphenylpropionate methobromide,
scopine 2-fluoro-2,2-diphenylacetate methobromide,
tropenol 2-fluoro-2,2-diphenylacetate methobromide;
tropenol 3,3',4,4'-tetrafluorobenzilate methobromide,
scopine 3,3',4,4'-tetrafluorobenzilate methobromide,
tropenol 4,4'-difluorobenzilate methobromide,
scopine 4,4'-difluorobenzilate methobromide,
tropenol 3,3'-difluorobenzilate methobromide,
scopine 3,3'-difluorobenzilate methobromide;
tropenol 9-hydroxy-fluorene-9-carboxylate methobromide;
tropenol 9-fluoro-fluorene-9-carboxylate methobromide;
scopine 9-hydroxy-fluorene-9-carboxylate methobromide;
scopine 9-fluoro-fluorene-9-carboxylate methobromide;
tropenol 9-methyl-fluorene-9-carboxylate methobromide;
scopine 9-methyl-fluorene-9-carboxylate methobromide;
cyclopropyltropine benzilate methobromide;
cyclopropyltropine 2,2-diphenylpropionate methobromide;
cyclopropyltropine 9-hydroxy-xanthene-9-carboxylate methobromide;
cyclopropyltropine 9-methyl-fluorene-9-carboxylate methobromide;
cyclopropyltropine 9-methyl-xanthene-9-carboxylate methobromide;
cyclopropyltropine 9-hydroxy-fluorene-9-carboxylate methobromide;
cyclopropyltropine methyl 4,4'-difluorobenzilate methobromide.
tropenol 9-hydroxy-xanthene-9-carboxylate methobromide;
scopine 9-hydroxy-xanthene-9-carboxylate methobromide;
tropenol 9-methyl-xanthene-9-carboxylate-methobromide;
scopine 9-methyl-xanthene-9-carboxylate-methobromide;
tropenol 9-ethyl-xanthene-9-carboxylate methobromide;
tropenol 9-difluoromethyl-xanthene-9-carboxylate methobromide;
scopine 9-hydroxymethyl-xanthene-9-carboxylate methobromide, The above-mentioned compounds may also be used as salts within the scope of the present invention, wherein instead of the methobromide the salts metho-X are used, wherein X may have the meanings given hereinbefore for X⁻.

As corticosteroids it is preferable to use compounds selected from among beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone, RPR-106541, NS-126, ST-26 and (S)-fluoromethyl 6,9-difluoro-17-[(2-furanylcarbonyl)oxy]-11-hydroxy-16-methyl-3-oxo-androsta-1,4-diene-17-carbothionate (S)-(2-oxo-tetrahydro-furan-3S-yl)6,9-difluoro-11-hydroxy-16-methyl-3-oxo-17-propionyloxy-androsta-1,4-diene-17-carbothionate, cyanomethyl 6α,9α-difluoro-11β-hydroxy-16α-methyl-3-oxo-17α-(2,2,3,3-tetramethylcyclopropylcarbonyl)oxy-androsta-1,4-diene-17β-carboxylate optionally in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof which may exist. Examples of possible salts and derivatives of the steroids may be: alkali metal salts, such as for example sodium or potassium salts, sulphobenzoates, phosphates, isonicotinates, acetates, dichloroacetates, propionates, dihydrogen phosphates, palmitates, pivalates or furoates.

PDE4-inhibitors which may be used are preferably compounds selected from among enprofyllin, theophyllin, roflumilast, ariflo (cilomilast), tofimilast, pumafentrin, lirimilast, arofyllin, atizoram, D-4418, Bay-198004, BY343, CP-325.366, D-4396 (Sch-351591), AWD-12-281 (GW-842470), NCS-613, CDP-840, D-4418, PD-168787, T-440, T-2585, V-11294A, Cl-1018, CDC-801, CDC-3052, D-22888, YM-58997, Z-15370 and
N-(3,5-dichloro-1-oxo-pyridin-4-yl)-4-difluoromethoxy-3-cyclopropylmethoxybenzamide
(−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide
(R)-(+)-1-(4-bromobenzyl)-4-[(3-cyclopentyloxy)-4-methoxyphenyl]-2-pyrrolidone
3-(cyclopentyloxy-4-methoxyphenyl)-1-(4-N'—[N-2-cyano-S-methyl-isothioureido]benzyl)-2-pyrrolidone cis[4-cyano-4-(3-cyclopentyloxy-4-methoxyphenyl)cyclohexane-1-carboxylic acid]
2-carbomethoxy-4-cyano-4-(3-cyclopropylmethoxy-4-difluoromethoxy-phenyl)cyclohexan-1-one
cis[4-cyano-4-(3-cyclopropylmethoxy-4-difluoromethoxyphenyl)cyclohexan-1-ol]
(R)-(+)-ethyl[4-(3-cyclopentyloxy-4-methoxyphenyl)pyrrolidin-2-ylidene]acetate
(S)-(−)-ethyl[4-(3-cyclopentyloxy-4-methoxyphenyl)pyrrolidin-2-ylidene]acetate
9-cyclopentyl-5,6-dihydro-7-ethyl-3-(2-thienyl)-9H-pyrazolo[3,4-c]-1,2,4-triazolo[4,3-a]pyridine
9-cyclopentyl-5,6-dihydro-7-ethyl-3-(tert-butyl)-9H-pyrazolo[3,4-c]-1,2,4-triazolo[4,3-a]pyridine optionally in the form of the racemates, enantiomers or diastereomers thereof and optionally in the form of the pharmacologically acceptable acid addition salts thereof, the solvates and/or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The LTD4-antagonists used are preferably compounds selected from among montelukast, pranlukast, zafirlukast, MCC-847 (ZD-3523), MN-001, MEN-91507 (LM-1507), VUF-5078, VUF-K-8707, L-733321 and
1-(((R)-3-(2-(6,7-difluoro-2-quinolinyl)ethenyl)phenyl)-3-(2-(2-hydroxy-2-propyl)phenyl)thio)methylcyclopropane-acetic acid,
1-(((1(R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid
[2-[[2-(4-tert-butyl-2-thiazolyl)-5-benzofuranyl]oxymethyl]phenyl]acetic acid optionally in the form of the racemates, enantiomers or diastereomers thereof and optionally in the form of the pharmacologically acceptable acid addition salts, solvates and/or hydrates thereof. According to the invention the acid addition salts of the betamimetics are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate. By salts or derivatives which the LTD4-antagonists may optionally be capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

EGFR-inhibitors which may be used are preferably compounds selected from among cetuximab, trastuzumab, ABX-EGF, Mab ICR-62 and
4-[(3-chloro-4-fluorophenyl)amino]-6-{[4-(morpholin-4-yl)-1-oxo-2-buten-1-yl]amino}-7-cyclopropylmethoxy-quinazoline
4-[(3-chloro-4-fluorophenyl)amino]-6-{[4-(N,N-diethyl-amino)-1-oxo-2-buten-1-yl]amino}-7-cyclopropyl-methoxy-quinazoline
4-[(3-chloro-4-fluorophenyl)amino]-6-{[4-(N,N-dimethyl-amino)-1-oxo-2-buten-1-yl]amino}-7-cyclopropyl-methoxy-quinazoline
4-[(R)-(1-phenyl-ethyl)amino]-6-{[4-(morpholin-4-yl)-1-oxo-2-buten-1-yl]amino}-7-cyclopentyloxy-quinazoline
4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline
4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline
4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline
4-[(3-chloro-4-fluoro-phenyl)amino]-6-[2-((S)-6-methyl-2-oxo-morpholin-4-yl)-ethoxy]-7-methoxy-quinazoline
4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline
4-[(3-chloro-4-fluorophenyl)amino]-6-{[4-(N,N-dimethyl-amino)-1-oxo-2-buten-1-yl]amino}-7-cyclopentyloxy-quinazoline
4-[(R)-(1-phenyl-ethyl)amino]-6-{[4-(N,N-to-(2-methoxy-ethyl)-amino]-1-oxo-2-buten-1-yl}amino}-7-cyclopropylmethoxy-quinazoline
4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline
4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline
4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline
4-[(3-chloro-4-fluorophenyl)amino]-6-{[4-(N,N-dimethyl-amino)-1-oxo-2-buten-1-yl]amino}-7-((R)-tetrahydrofuran-3-yloxy)-quinazoline
4-[(3-chloro-4-fluorophenyl)amino]-6-{[4-(N,N-dimethyl-amino)-1-oxo-2-buten-1-yl]amino}-7-((S)-tetrahydrofuran-3-yloxy)-quinazoline
4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline
4-[(3-chloro-4-fluorophenyl)amino]-6-{[4-(N-cyclopropyl-N-methyl-amino)-1-oxo-2-buten-1-yl]amino}-7-cyclopentyloxy-quinazoline
4-[(3-chloro-4-fluorophenyl)amino]-6-{[4-(N,N-dimethyl-amino)-1-oxo-2-buten-1-yl]amino}-7-[(R)-(tetrahydrofuran-2-yl)methoxy]-quinazoline
4-[(3-chloro-4-fluorophenyl)amino]-6-{[4-(N,N-dimethyl-amino)-1-oxo-2-buten-1-yl]amino}-7-[(S)-(tetrahydrofuran-2-yl)methoxy]-quinazoline
4-[(3-ethynyl-phenyl)amino]-6,7-to-(2-methoxy-ethoxy)-quinazoline
4-[(3-chloro-4-fluorophenyl)amino]-7-[3-(morpholin-4-yl)-propyloxy]-6-[(vinyl-carbonyl)amino]-quinazoline
4-[(R)-(1-phenyl-ethyl)amino]-6-(4-hydroxy-phenyl)-7H-pyrrolo[2,3-d]pyrimidine
3-cyano-4-[(3-chloro-4-fluorophenyl)amino]-6-{[4-(N,N-dimethylamino)-1-oxo-2-buten-1-yl]amino}-7-ethoxy-quinoline
4-{[3-chloro-4-(3-fluoro-benzyloxy)-phenyl]amino}-6-(5-{[(2-methanesulphonyl-ethyl)amino]methyl}-furan-2-yl)quinazoline
4-[(R)-(1-phenyl-ethyl)amino]-6-{[4-((R)-6-methyl-2-oxo-morpholin-4-yl)-1-oxo-2-buten-1-yl]amino}-7-methoxy-quinazoline
4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline 4-[(3-chloro-4-fluorophenyl)amino]-6-({4-[N,N-to-(2-methoxy-ethyl)-amino]-1-oxo-2-buten-1-yl}amino)-7-[(tetrahydrofuran-2-yl)methoxy]-quinazoline 4-[(3-ethynyl-phenyl)amino]-6-{[4-(5,5-dimethyl-2-oxo-morpholin-4-yl)-1-oxo-2-buten-1-yl]amino}-quinazoline 4-[(3-chloro-4-fluoro-phenyl)amino]-6-[2-(2,2-dimethyl-6-oxo-morpholin-4-yl)-ethoxy]-7-methoxy-quinazoline 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline 4-[(3-chloro-4-fluoro-phenyl)amino]-6-{2-[4-(2-oxo-morpholin-4-yl)-piperidin-1-yl]-ethoxy}-7-methoxy-quinazoline 4-[(3-chloro-4-fluoro-phenyl)amino]-6-[1-(tert.-butyloxycarbonyl)-piperidin-4-yloxy]-7-methoxy-quinazoline 4-[(3-chloro-4-fluoro-phenyl)amino]-6-(trans-4-amino-cyclohexan-1-yloxy)-7-methoxy-quinazoline 4-[(3-chloro-4-fluoro-phenyl)amino]-6-(trans-4-methanesulphonylamino-cyclohexan-1-yloxy)-7-methoxy-quinazoline 4-[(3-chloro-4-fluoro-phenyl)amino]-6-(tetrahydropyran-3-yloxy)-7-methoxy-quinazoline 4-[(3-chloro-4-fluoro-phenyl)amino]-6-(1-methyl-piperidin-4-yloxy)-7-methoxy-quinazoline 4-[(3-chloro-4-fluoro-phenyl)amino]-6-{1-[(morpholin-4-yl)carbonyl]-piperidin-4-yl-oxy}-7-methoxy-quinazoline 4-[(3-chloro-4-fluoro-phenyl)amino]-6-{1-[(methoxymethyl)carbonyl]-piperidin-4-yl-oxy}-7-methoxy-quinazoline 4-[(3-chloro-4-fluoro-phenyl)amino]-6-(piperidin-3-yloxy)-7-methoxy-quinazoline 4-[(3-chloro-4-fluoro-phenyl)amino]-6-[1-(2-acetylamino-ethyl)-piperidin-4-yloxy]-7-methoxy-quinazoline 4-[(3-chloro-4-fluoro-phenyl)amino]-6-(tetrahydropyran-4-yloxy)-7-ethoxy-quinazoline 4-[(3-chloro-4-fluoro-phenyl)amino]-6-((S)-tetrahydrofuran-3-yloxy)-7-hydroxy-quinazoline 4-[(3-chloro-4-fluoro-phenyl)amino]-6-(tetrahydropyran-4-yloxy)-7-(2-methoxy-ethoxy)-quinazoline 4-[(3-chloro-4-fluoro-phenyl)amino]-6-{trans-4-[(dimethylamino)sulphonylamino]-cyclohexan-1-yloxy}-7-methoxy-quinazoline 4-[(3-chloro-4-fluoro-phenyl)amino]-6-{trans-4-[(morpholin-4-yl)carbonylamino]-cyclohexan-1-yloxy}-7-methoxy-quinazoline 4-[(3-chloro-4-fluoro-phenyl)amino]-6-{trans-4-[(morpholin-4-yl)sulphonylamino]-cyclohexan-1-yloxy}-7-methoxy-quinazoline 4-[(3-chloro-4-fluoro-phenyl)amino]-6-(tetrahydropyran-4-yloxy)-7-(2-acetylamino-ethoxy)-quinazoline 4-[(3-chloro-4-fluoro-phenyl)amino]-6-(tetrahydropyran-4-yloxy)-7-(2-methanesulphonylamino-ethoxy)-quinazoline 4-[(3-chloro-4-fluoro-phenyl)amino]-6-{1-[(piperidin-1-yl)carbonyl]-piperidin-4-yloxy}-7-methoxy-quinazoline 4-[(3-chloro-4-fluoro-phenyl)amino]-6-(1-aminocarbonylmethyl-piperidin-4-yloxy)-7-methoxy-quinazoline 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline 4-[(3-chloro-4-fluoro-phenyl)amino]-6-(trans-4-ethanesulphonylamino-cyclohexan-1-yloxy)-7-methoxy-quinazoline 4-[(3-chloro-4-fluoro-phenyl)amino]-6-(1-methanesulphonyl-piperidin-4-yloxy)-7-ethoxy-quinazoline 4-[(3-chloro-4-fluoro-phenyl)amino]-6-(1-methanesulphonyl-piperidin-4-yloxy)-7-(2-methoxy-ethoxy)-quinazoline 4-[(3-chloro-4-fluoro-phenyl)amino]-6-[1-(2-methoxy-acetyl)-piperidin-4-yloxy]-7-(2-methoxy-ethoxy)-quinazoline 4-[(3-chloro-4-fluoro-phenyl)amino]-6-(cis-4-acetylamino-cyclohexan-1-yloxy)-7-methoxy-quinazoline 4-[(3-ethynyl-phenyl)amino]-6-[1-(tert.-butyloxycarbonyl)-piperidin-4-yloxy]-7-methoxy-quinazoline 4-[(3-ethynyl-phenyl)amino]-6-(tetrahydropyran-4-yloxy]-7-methoxy-quinazoline 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline 4-[(3-chloro-4-fluoro-phenyl)amino]-6-{cis-4-[(morpholin-4-yl)carbonylamino-cyclohexan-1-yloxy}-7-methoxy-quinazoline 4-[(3-chloro-4-fluoro-phenyl)amino]-6-{1-[2-(2-oxopyrrolidin-1-yl)ethyl]-piperidin-4-yloxy}-7-methoxy-quinazoline 4-[(3-chloro-4-fluoro-phenyl)amino]-6-{1-[(morpholin-4-yl)carbonyl]-piperidin-4-yloxy}-7-(2-methoxy-ethoxy)-quinazoline 4-[(3-ethynyl-phenyl)amino]-6-(1-acetyl-piperidin-4-yloxy)-7-methoxy-quinazoline 4-[(3-ethynyl-phenyl)amino]-6-(1-methyl-piperidin-4-yloxy)-7-methoxy-quinazoline 4-[(3-ethynyl-phenyl)amino]-6-(1-methanesulphonyl-piperidin-4-yloxy)-7-methoxy-quinazoline 4-[(3-chloro-4-fluoro-phenyl)amino]-6-(1-methyl-piperidin-4-yloxy)-7(2-methoxy-ethoxy)-quinazoline 4-[(3-chloro-4-fluoro-phenyl)amino]-6-(1-isopropyloxycarbonyl-piperidin-4-yloxy)-7-methoxy-quinazoline 4-[(3-chloro-4-fluoro-phenyl)amino]-6-(cis-4-methylamino-cyclohexan-1-yloxy)-7-methoxy-quinazoline 4-[(3-chloro-4-fluoro-phenyl)amino]-6-{cis-4-[N-(2-methoxy-acetyl)-N-methyl-amino]-cyclohexan-1-yloxy}-7-methoxy-quinazoline 4-[(3-ethynyl-phenyl)amino]-6-(piperidin-4-yloxy)-7-methoxy-quinazoline 4-[(3-ethynyl-phenyl)amino]-6-[1-(2-methoxy-acetyl)-piperidin-4-yloxy]-7-methoxy-quinazoline 4-[(3-ethynyl-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(cis-2,6-dimethyl-morpholin-4-yl)carbonyl]-piperidin-4-yloxy}-7-methoxy-quinazoline 4-[(3-chloro-4-fluoro-phenyl)amino]-6-{1-[(2-methyl-morpholin-4-yl)carbonyl]-piperidin-4-yloxy}-7-methoxy-quinazoline 4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline 4-[(3-chloro-4-fluoro-phenyl)amino]-6-{1-[(N-methyl-N-2-methoxyethyl-amino)carbonyl]-piperidin-4-yloxy}-7-methoxy-quinazoline 4-[(3-chloro-4-fluoro-phenyl)amino]-6-(1-ethyl-piperidin-4-yloxy)-7-methoxy-quinazoline 4-[(3-chloro-4-fluoro-phenyl)amino]-6-{1-[(2-methoxyethyl)carbonyl]-piperidin-4-yloxy}-7-methoxy-quinazoline 4-[(3-chloro-4-fluoro-phenyl)amino]-6-{1-[(3-methoxypropyl-amino)-carbonyl]-piperidin-4-yloxy}-7-methoxy-quinazoline 4-[(3-chloro-4-fluoro-phenyl)amino]-6-[cis-4-(N-methanesulphonyl-N-methyl-amino)-cyclohexan-1-yloxy]-7-methoxy-quinazoline 4-[(3-chloro-4-fluoro-phenyl)amino]-6-[cis-4-(N-acetyl-N-methyl-amino)-cyclohexan-1-yloxy]-7-methoxy-quinazoline 4-[(3-chloro-4-fluoro-phenyl)amino]-6-(trans-4-methylamino-cyclohexan-1-yloxy)-7-methoxy-quinazoline 4-[(3-chloro-4-fluoro-phenyl)amino]-6-[trans-4-(N-methanesulphonyl-N-methyl-amino)-cyclohexan-1-yloxy]-7-methoxy-quinazoline 4-[(3-chloro-4-fluoro-phenyl)amino]-6-(trans-4-dimethylamino-cyclohexan-1-yloxy)-7-methoxy-quinazoline 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline 4-[(3-chloro-4-fluoro-phenyl)amino]-6-(1-methanesulphonyl-piperidin-4-yloxy)-7-methoxy-quinazoline 4-[(3-chloro-4-fluoro-phenyl)amino]-6-(1-cyano-piperidin-4-yloxy)-7-methoxy-quinazoline optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The dopamine agonists used are preferably compounds selected from among bromocriptin, cabergoline, alpha-dihydroergocryptine, lisuride, pergolide, pramipexol, roxindol, ropinirol, talipexol, tergurid and viozan, optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

H1-Antihistamines which may be used are preferably compounds selected from among epinastine, cetirizine, azelastine, fexofenadine, levocabastine, loratadine, mizolastine, ketotifen, emedastine, dimetindene, clemastine, bamipine, cexchlorpheniramine, pheniramine, doxylamine, chlorophenoxamine, dimenhydrinate, diphenhydramine, promethazine, ebastine, desloratidine and meclozine, optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

It is also possible to use inhalable macromolecules, as disclosed in EP 1 003 478 A1 or CA 2297174 A1.

In addition, the compounds may come from the groups of ergot alkaloid derivatives, the triptans, the CGRP-inhibitors, the phosphodiesterase-V inhibitors, optionally in the form of the racemates, enantiomers or diastereomers thereof, optionally in the form of the pharmacologically acceptable acid addition salts, the solvates and/or hydrates thereof.

Examples of ergot alkaloid derivatives are dihydroergotamine and ergotamine.

What is claimed is:

1. Inhaler for active dispensing of an inhalation formulation as an aerosol, comprising:

a conveying means for at least one of conveying and nebulizing the inhalation formulation for generating the aerosol and having a nozzle for dispensing of the formulation, and a mouthpiece coaxially surrounding the nozzle and provided with at least one fluidically connected or associated air supply opening for enabling ambient air to be drawn into the mouthpiece at a location upstream of said nozzle in a direction of flow toward an outlet end of the mouthpiece, wherein a flow path for the ambient air into said mouthpiece from the at least one air supply opening extends from the at least one air supply opening within a space between an inner wall of the mouthpiece and the nozzle around the outside of said nozzle toward an open end thereof and has a total flow resistance of at least 60,000 $Pa^{1/2}s/m^3$, and wherein the flow resistance is produced at least in part by a replaceable apertured insert plate that has openings with a fixed flow-through cross section and that is clampingly engages against the inner wall of the mouthpiece with an outwardly flaring sealing lip that is mounted on an outer edge of the apertured insert plate and at a protrusion of the nozzle; and wherein the sealing lip is radially and axially inclined in a direction away from the insert plate and toward said mouthpiece.

2. Inhaler according to claim 1, wherein the at least one air supply opening has a flow resistance of at least 75,000 $Pa^{1/2}s/m^3$.

3. Inhaler according to claim 1, wherein the at least one air supply opening has a flow resistance of about 90,000-96,000 $Pa^{1/2}s/m^3$.

4. Inhaler according to claim 1, wherein the flow resistance is produced in part by the size of the air supply openings without any flow varying valve structure being associated with the air supply openings.

5. Inhaler according to claim 1, wherein the inhaler comprises a pressure generator as conveying means.

6. Inhaler according to claim 1, wherein the inhaler comprises an insertable reservoir containing the inhalation formulation.

7. Inhaler according to claim 1, wherein the conveying means generates the aerosol, at least after start of the generation, independent on any sucking or breathing-in via the mouthpiece.

8. Inhaler according to claim 1, wherein ambient air is sucked into or flows into the mouthpiece through said at least on air supply opening when air and the aerosol are sucked via the mouthpiece.

9. Inhaler according to claim 1, wherein the replaceable apertured insert plate is adapted for mounting in the mouthpiece of an assembled inhaler.

10. Inhaler according to claim 1, wherein a flow resistance of at least 75,000 $Pa^{1/2}$ $s/m^3$ is produced by at least said insert plate.

11. Inhaler according to claim 1, wherein the flow resistance is produced by the size of at least one air supply opening in conjunction with said insert plate.

12. Inhaler according to claim 1, wherein the insert plate comprises at least one hole for adjusting the flow resistance, and wherein the at least one hole is only a single opening that has a diameter of 3.2 to 3.6 mm, the diameter being a circular aerodynamic cross section corresponding in its effect.

13. Inhaler according to claim 1, wherein the insert plate comprises at least one hole for adjusting the flow resistance, and wherein the at least one hole is two openings each of which has a diameter of 2.2 to 2.6 mm, the diameter being a circular aerodynamic cross section corresponding in its effect.

14. Inhaler according to claim 1, wherein the insert plate comprises at least one hole for adjusting the flow resistance, and wherein the at least one hole is three openings each of which has a diameter of 1.8 to 2.1 mm, the diameter being a circular aerodynamic cross section corresponding in its effect.

15. Inhaler according to claim 1, wherein the insert comprises at least one hole for adjusting the flow resistance, and wherein the at least one hole is four openings each of which diameter 1.5 to 1.8 mm, the diameter being a circular aerodynamic cross section corresponding in its effect.

16. Inhaler for actively dispensing of an inhalation formulation as an aerosol, comprising:

a conveying means for at least one of conveying and nebulizing the inhalation formulation as the aerosol and having a nozzle for dispensing of the formulation, and a mouthpiece coaxially surrounding the nozzle and with at least one fluidically connected or associated ambient air supply opening which enables air to enter the mouthpiece at a location upstream of said nozzle in a direction of flow toward an outlet end of the mouthpiece, wherein the inhaler comprises an insert located within the mouthpiece between the at least one ambient air supply opening and an outlet end of said nozzle to define or increase the flow resistance to air entering through the at least one air supply opening as it flows toward an outlet end of the nozzle within a space between the inside of the mouthpiece and the nozzle, wherein the insert is replaceably mountable in the mouthpiece, and wherein the insert comprises an apertured plate having at least one hole having a fixed flow-though cross section and at least one fixed guiding element which overlies the at least one hole at a distance and which blocks a direct or straight flow of ambient air from the at least one hole toward the outlet end of the mouthpiece, the guiding element being formed of one piece with the apertured plate.

17. Inhaler according to claim 16, wherein the inhaler comprises a pressure generator as the conveying means.

18. Inhaler according to claim 16, wherein the inhaler comprises an insertable reservoir.

19. Inhaler according to claim 16, wherein the conveying means is adapted for generating the aerosol, at least after start of the generation, independent on any sucking or breathing-in via the mouthpiece.

20. Inhaler according to claim 16, wherein ambient air is sucked into or flows into the mouthpiece through said at least one air supply opening and across said insert when air and the aerosol are sucked via the mouthpiece.

* * * * *